(12) United States Patent  (10) Patent No.: US 8,704,688 B2
Shen et al. (45) Date of Patent: Apr. 22, 2014

(54) IMPLANTABLE MEDICAL DEVICE DIAGNOSTIC DATA ACQUISITION AND STORAGE

(75) Inventors: Zhe Shen, New Brighton, MN (US); Joseph E. Bange, Eagan, MN (US); Allan T. Koshiol, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 93 days.

(21) Appl. No.: 13/425,148

(22) Filed: Mar. 20, 2012

(65) Prior Publication Data

US 2012/0179058 A1    Jul. 12, 2012

Related U.S. Application Data

(63) Continuation of application No. 12/791,068, filed on Jun. 1, 2010, now Pat. No. 8,200,324, which is a continuation of application No. 11/470,201, filed on Sep. 5, 2006, now Pat. No. 7,756,573.

(51) Int. Cl.
*H03M 7/30* (2006.01)

(52) U.S. Cl.
USPC .............................. 341/87; 607/32

(58) Field of Classification Search
USPC ................ 341/87; 607/32, 27, 17, 30, 9, 3; 600/523, 509, 481
See application file for complete search history.

(56) References Cited

U.S. PATENT DOCUMENTS

| | | | |
|---|---|---|---|
| 4,583,553 A | 4/1986 | Shah et al. |
| 4,716,903 A | 1/1988 | Hansen et al. |
| 4,726,380 A | 2/1988 | Vollmann et al. |
| 4,814,974 A | 3/1989 | Narayanan et al. |
| 4,920,489 A | 4/1990 | Hubelbank et al. |
| 4,945,477 A | 7/1990 | Edwards |
| 5,002,062 A | 3/1991 | Suzuki |
| 5,007,431 A | 4/1991 | Donehoo |
| 5,052,399 A | 10/1991 | Olive et al. |
| 5,215,098 A | 6/1993 | Steinhaus et al. |
| 5,217,021 A | 6/1993 | Steinhaus et al. |
| 5,255,186 A | 10/1993 | Steinhaus et al. |
| 5,263,486 A | 11/1993 | Jeffreys |
| 5,309,919 A | 5/1994 | Snell et al. |
| 5,311,867 A | 5/1994 | Kynor |
| 5,312,446 A | 5/1994 | Holschbach et al. |
| 5,313,953 A | 5/1994 | Yomtov et al. |
| 5,331,966 A | 7/1994 | Bennett et al. |
| 5,333,615 A | 8/1994 | Craelius et al. |

(Continued)

OTHER PUBLICATIONS

Gilkson et al. "The Implantable Cardioverter Defibrillator", The Lancet, Apr. 7, 2001, pp. 1107-1117, vol. 357.

(Continued)

*Primary Examiner* — Joseph Lauture
(74) *Attorney, Agent, or Firm* — Faegre Baker Daniels LLP

(57) ABSTRACT

Physiological data is generated from signals received from one or more leads associated with the IMD. The physiological data is sampled to generate a plurality of data samples. A predictive encoding algorithm is applied to the plurality of data samples to generate a plurality of encoded data samples each corresponding to one of the plurality of data samples. An entropy encoding algorithm is then applied to the plurality of encoded data samples to generate a plurality of code words each corresponding to one of the plurality of encoded data samples. The code words are then stored in a memory in the IMD.

17 Claims, 12 Drawing Sheets

(56) References Cited

U.S. PATENT DOCUMENTS

| | | | |
|---|---|---|---|
| 5,354,315 A | 10/1994 | Armstrong | |
| 5,354,316 A | 10/1994 | Keimel | |
| 5,442,351 A | 8/1995 | Horspool et al. | |
| 5,507,780 A | 4/1996 | Finch | |
| 5,518,001 A | 5/1996 | Snell | |
| 5,545,186 A | 8/1996 | Olson et al. | |
| 5,603,331 A | 2/1997 | Heemels et al. | |
| 5,623,935 A | 4/1997 | Faisandier | |
| 5,709,216 A | 1/1998 | Woodson, III | |
| 5,722,999 A * | 3/1998 | Snell | 607/32 |
| 5,732,708 A | 3/1998 | Nau et al. | |
| 5,776,168 A | 7/1998 | Gunderson | |
| 5,779,634 A | 7/1998 | Ema et al. | |
| 5,782,885 A | 7/1998 | Andersson | |
| 5,785,660 A | 7/1998 | van Lake et al. | |
| 5,794,624 A | 8/1998 | Kwong | |
| 5,817,134 A | 10/1998 | Greenhut et al. | |
| 5,819,740 A | 10/1998 | Muhlenberg | |
| 5,836,889 A | 11/1998 | Wyborny et al. | |
| 5,836,982 A | 11/1998 | Muhlenberg et al. | |
| 5,908,392 A | 6/1999 | Wilson et al. | |
| 5,935,081 A | 8/1999 | Kadhiresan | |
| 6,009,472 A | 12/1999 | Boudou et al. | |
| 6,161,043 A | 12/2000 | McClure et al. | |
| 6,236,882 B1 | 5/2001 | Lee et al. | |
| 6,253,260 B1 | 6/2001 | Beardsley et al. | |
| 6,346,245 B1 | 2/2002 | Walther et al. | |
| 6,453,201 B1 | 9/2002 | Daum et al. | |
| 6,526,314 B1 | 2/2003 | Eberle et al. | |
| 6,584,354 B1 | 6/2003 | Mann et al. | |
| 6,589,187 B1 | 7/2003 | Dirnberger et al. | |
| 6,599,242 B1 | 7/2003 | Splett et al. | |
| 6,622,050 B2 | 9/2003 | Thompson | |
| 6,628,985 B2 | 9/2003 | Sweeney et al. | |
| 6,650,939 B2 | 11/2003 | Taepke, II et al. | |
| 6,719,689 B2 | 4/2004 | Munneke et al. | |
| 6,754,795 B2 | 6/2004 | Chen et al. | |
| 6,778,859 B2 | 8/2004 | Graindorge | |
| 6,823,210 B2 | 11/2004 | Eberle et al. | |
| 6,865,424 B2 | 3/2005 | Daum et al. | |
| 6,910,084 B2 | 6/2005 | Augustijn et al. | |
| 6,933,837 B2 | 8/2005 | Gunderson et al. | |
| 6,961,617 B1 | 11/2005 | Snell | |
| 7,016,721 B2 | 3/2006 | Lee et al. | |
| 7,027,872 B2 | 4/2006 | Thompson | |
| 7,130,678 B2 | 10/2006 | Ritscher et al. | |
| 7,484,129 B1 | 1/2009 | Varrichio | |
| 7,756,573 B2 | 7/2010 | Shen et al. | |
| 8,200,324 B2 | 6/2012 | Shen et al. | |
| 2001/0027331 A1 | 10/2001 | Thompson | |
| 2001/0039437 A1 | 11/2001 | Taepke, II et al. | |
| 2002/0026122 A1 | 2/2002 | Lee et al. | |
| 2002/0077563 A1 | 6/2002 | Sweeney et al. | |
| 2002/0193668 A1 | 12/2002 | Munneke et al. | |
| 2002/0193847 A1 | 12/2002 | Daum et al. | |
| 2003/0135125 A1 | 7/2003 | Lu et al. | |
| 2003/0141965 A1 | 7/2003 | Gunderson et al. | |
| 2003/0187365 A1 | 10/2003 | Eberle et al. | |
| 2004/0059391 A1 | 3/2004 | Sweeney et al. | |
| 2004/0215270 A1 | 10/2004 | Ritscher et al. | |
| 2005/0060186 A1 | 3/2005 | Blowers et al. | |
| 2005/0065815 A1 | 3/2005 | Mazar et al. | |
| 2005/0131492 A1 | 6/2005 | Kroll et al. | |
| 2005/0240236 A1 | 10/2005 | Daum et al. | |
| 2005/0261934 A1 | 11/2005 | Thompson | |
| 2006/0287691 A1 | 12/2006 | Drew | |
| 2008/0051861 A1 | 2/2008 | Cross et al. | |
| 2010/0234914 A1 | 9/2010 | Shen et al. | |

OTHER PUBLICATIONS

Nowak et al., "Diagnostic Value of Onset-Recordings and Marker Annotations in Dual Chamber Pacemaker Stored Electrograms", The European Society of Cardiology, Eurospace, Jan. 2003, pp. 103-109, vol. 5, published by Elsevier Science Ltd.

* cited by examiner

IMPLANTABLE MEDICAL DEVICE DIAGNOSTIC DATA ACQUISITION AND STORAGE

CROSS REFERENCE TO RELATED APPLICATION

This application is a continuation of U.S. patent application Ser. No. 12/791,068, filed Jun. 1, 2010, titled IMPLANTABLE MEDICAL DEVICE DIAGNOSTIC DATA ACQUISITION AND STORAGE, which is a continuation of U.S. patent application Ser. No. 11/470,201, filed Sep. 5, 2006, titled IMPLANTABLE MEDICAL DEVICE DIAGNOSTIC DATA ACQUISITION AND STORAGE, now U.S. Pat. No. 7,756,573, which are incorporated herein by reference in their entirety.

TECHNICAL FIELD

The present invention relates generally to acquisition and storage of data in implantable medical devices. More specifically, the present invention relates to a memory management system for implantable medical devices.

BACKGROUND

Medical devices are implanted in the bodies of patients for various purposes such as heart rhythm management and stimulation. Implantable cardioverter-defibrillators (ICDs), for example, monitor for certain irregular events in the heart, such as cardiac arrhythmia, ventricular fibrillation, and ventricular tachycardia, and administer therapy in response to detection of an irregular event. For example, when cardiac arrhythmia is detected, the ICD delivers a large jolt of electricity to cause the heart to begin beating in a more regular pattern. In addition to monitoring for conditions and delivering therapy, modern ICDs store a number of types of data that may be retrieved later by a doctor (or other medical personnel), so that the doctor can better understand the circumstances of irregular heart events in the patient.

For example, ICDs often store cardiac electrogram (EGM) data, which may be relevant to preconditions of an irregular heart event and/or the response to administered therapy. In addition, post therapy EGM is typically recorded to allow the physician to assess the therapy prescribed and possibly fine tune therapy parameters. Of course, the more information the doctor has, the better his/her understanding of the circumstances will be, and the better his/her medical decisions will typically be. A doctor would like to be able to access and analyze relevant medical data (e.g., EGM data) spanning a fairly long period of time, in order to detect preconditions, patterns, responses, and other indications.

However, as with all devices, ICDs have only limited memory with which to store data. As such, a certain finite amount of medical data can be stored and provided to medical personnel. Typically, the amount of memory available for storing data pertaining to irregular heart conditions is on the order of several hundred kilobytes. Memory limitations in conventional ICDs (and other therapeutic IMDs) can seriously impact the overall design and functionality of ICDs. In an attempt to cope with memory limitations, for example, designers of conventional ICDs typically implement various memory management processes that are often suboptimal.

Even if more memory were to be provided in an ICD, this does alone not solve the problems associated with storing medical data in a way that facilitates optimal memory usage. In attempting to store more and more data associated with irregular heart events, ICD memory is often exhausted very quickly. For example, conventional systems often store duplicative or redundant data because the data is relevant to multiple events that occur at the same time. Clearly, redundant storage of data is a poor use of limited memory. On the other hand, data that is relevant to multiple events should be accessible for analysis of each of those events. As such, limited memory in ICDs and other implantable medical devices should be used more efficiently than in conventional systems, while storing the most medically relevant data possible.

SUMMARY

Discussed herein are memory management systems and methods for implantable medical devices.

In one aspect, a method for processing data in an implantable medical device (IMD) includes generating physiological data from signals received from one or more leads associated with the IMD, and sampling the physiological data to generate a plurality of data samples. A predictive encoding algorithm then applied to the plurality of data samples to generate a plurality of encoded data samples each corresponding to one of the plurality of data samples. An entropy encoding algorithm is applied to the plurality of encoded data samples to generate a plurality of code words each corresponding to one of the plurality of encoded data samples. The code words are then stored in a memory in the IMD.

In another aspect, an implantable medical device (IMD) includes one or more leads configured to sense physiological signals, a processor, and a memory. The processor is configured to generate physiological data from the physiological signals received from one or more leads associated with the IMD, and sample the physiological data to generate a plurality of data samples. The processor is also configured apply a predictive encoding algorithm to the plurality of data samples to generate a plurality of encoded data samples each corresponding to one of the plurality of data samples. The processor is further configured to apply an entropy encoding algorithm to the plurality of encoded data samples to generate a plurality of code words each corresponding to one of the plurality of encoded data samples. The memory is configured to store the code words.

In a further aspect, an implantable medical device (IMD) comprising includes a memory configured to store a prioritization schedule of physiological episodes. The prioritization schedule specifies a priority for each of a plurality of types of physiological episodes, a minimum number indicating a minimum number of data sets to be recorded for each of the physiological episodes, and a maximum number indicating a maximum number of data sets to be recorded for each of the physiological episodes. The IMD also includes a processor configured to delete a first recorded set of diagnostic data associated with a type of physiological episode of a first priority, only if a second received set of diagnostic data is associated with a type of physiological episode of a second priority that is higher than the first priority, and deletion of the first set of diagnostic data would not result in fewer sets of diagnostic data than the minimum number specified for the type of episode associated with the first set of diagnostic data.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the scope of the present invention. Accordingly, the drawings and detailed description are to be regarded as illustrative in nature and not restrictive.

Figure 1:
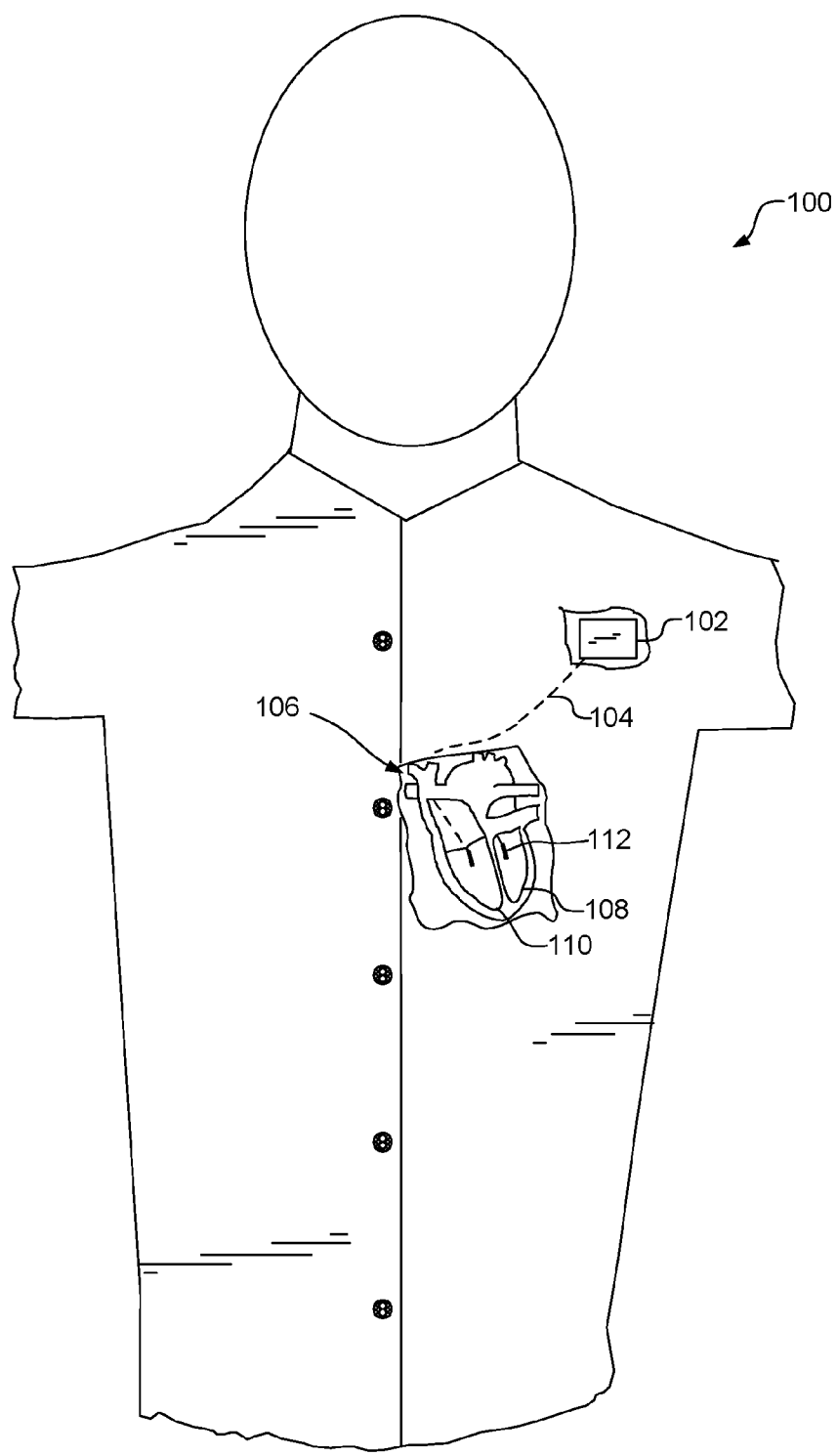
FIG. 1 illustrates a torso of a human patient with an implantable cardioverter-defibrillator (ICD) in accordance with one embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

An implantable medical device (IMD) generally refers to any medical device that can be implanted in a human body to perform one or more of a sensing function or a therapeutic function. By way of example, but not limitation, an IMD may be operable to sense a physiologic parameter, such as blood pressure, temperature, posture, blood sugar level, or others. Some IMDs, such as implantable cardioverter-defibrillators (ICDs) and pacemakers (PMs), store electrogram (EGM) data. An IMD may be operable to provide therapy, such as, but not limited to, pulses for rhythm management in a patient's heart. In addition to sensing and therapy, an IMD may provide other functions, such as communications functions. For example, IMDs typically transmit stored data to external devices, such as an IMD programmer recorder/monitor (PRM) or in-home monitoring device.

Embodiments described herein generally provide for management of memory in an IMD. Systems and methods are described that manage the acquisition, storage, organization, and communication of data associated with an IMD. Some embodiments may be understood to include a platform or methodology for managing the data acquisition, storage, organization, and communication processes. Although embodiments described herein pertain to an ICD, it is to be understood that the memory management systems and methods may be more generally applied to any IMD in which diagnostic data is stored. For example, other embodiments may be implemented in a pacemaker (PM). In addition, although the embodiments herein pertain to electrogram (EGM) and marker data, it is to be understood that the systems and methods described herein could be applied to virtually any type of data.

FIG. 1 illustrates a torso of a human patient 100 in which an implantable cardioverter defibrillator (ICD) 102 has been implanted. The ICD 102 is located in the upper chest of the patient 100, and has insulated wire leads 104 that extend into the patient's heart 106 and are affixed at selected locations in the heart 106. For example, leads 104 may run through left and right chambers of the heart 106 and into the left ventricle 108 and the right ventricle 110. Distal ends 112 of the leads 108 are capable of picking up electrical energy that is generated in the heart 106 due to contractions and relaxation of the myocardium of the heart 106. The leads 104 communicate the heart's 106 electrical signals to the ICD 102.

The leads 104 are also used to administer therapy to the myocardium of the heart 106. When irregular heart episodes are detected, an electrical signal is typically sent through the leads 104 to cause the heart 106 to begin beating properly. Some of these irregular episodes are tachycardia, bradycardia, and fibrillation. In the case of bradycardia, the therapy administered to the heart 106 may consist of one or more pacing pulses to adjust the heart rate. In the case of fibrillation, the therapy administered to the heart 106 may consist of a large shock, to cause the heart to begin beating normally.

Figure 2:
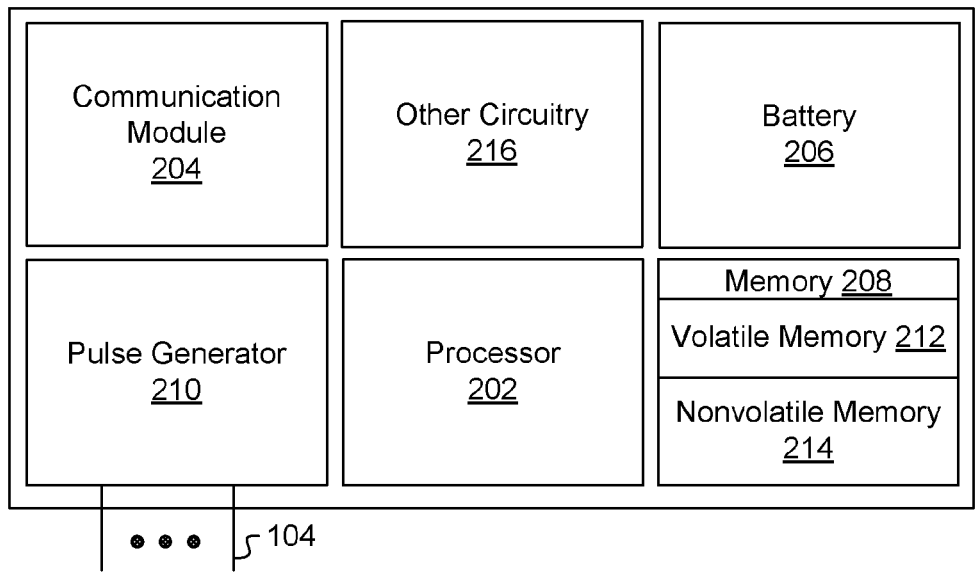
FIG. 2 is a schematic diagram illustrating exemplary components in a therapeutic implantable medical device (IMD), such as an ICD or a PM, in accordance with one embodiment.

FIG. 2 is a block diagram of the ICD 102, which illustrates components of the ICD 102 in accordance with one embodiment. The ICD 102 includes a processor 202, a communication module 204, a battery 206, a memory 208, a pulse generator 210, and other circuitry 216. The processor 202 executes instructions stored in the memory 208 that generally cause the processor 202 to control or facilitate the functions of the ICD 102 and/or components of the ICD 102. More specifically, the processor 202, in combination with other components, performs functions for managing memory 208 that stores diagnostic data in the ICD 102.

The memory 208 includes the volatile memory 212 and nonvolatile memory 214. In accordance with one embodiment, nonvolatile memory 214 stores code that includes bootstrap functions and device recovery operations, such as microprocessor reset. The nonvolatile memory 214 may also include calibration data and parameter data. The volatile memory 208 includes diagnostic data. The volatile memory 208 may also include microprocessor-executable code, operating parameters, status data, and/or other data.

In some embodiments, diagnostic data received on the leads 104 is continuously stored in a circular buffer in volatile memory 212. Diagnostic data can include, without limitation, electrogram (EGM) data, marker data, interval data, sensor data, or morphology data. As diagnostic data is received, the data is written over older data in the circular buffer. As discussed in more detail below, diagnostic data that is around the time of a detected cardiac episode may be moved from the circular buffer and into another part of memory 212, so that the diagnostic data is not written over, but rather is available for later analysis. For example, diagnostic data that is moved into another part of memory 212 for later use, may be provided to an external device (not shown) that is external to the patient 100. An external device refers to any device external to the patient's body that is telemetry enabled and capable of communicating with the IMD 102. As such, examples of external devices are PRMs, in-home monitoring devices, manufacturing test equipment, or wands.

Accordingly, the communication module 204 provides communication functionality so that the ICD 102 can communicate with an external device. The communication module 204 telemeters requested data to the external device. The communication module 204 communicates wirelessly using any of various wireless communication modes, such as magnetic, and/or radio frequency. As such, through the communication module 204, an external device can obtain diagnostic data stored in memory 208, such as, but not limited to, electrogram (EGM) data, marker data, and therapy administration data.

The pulse generator 210 generates pacing and/or shock pulses and receives electrical signals from the heart through multiple leads 104. Other circuitry 216 performs other functions such as, but not limited to, signal filtering and analysis. For example, the other circuitry 216 may analyze EGM data to identify heart beats. The battery 206 provides power to the components of the ICD 102. The battery 206 may or may not be rechargeable. The battery 206 typically is not capable of delivering the short burst of high charge that is required of a defibrillation shock. As such, in various embodiments, the pulse generator 210 includes a capacitor (not shown) that charges prior to delivery of a high-energy defibrillation shock.

As discussed, diagnostic data obtained through the leads 104 is analyzed to determine if various irregular cardiac episodes are occurring. A cardiac episode is any detectable heart condition or behavior of interest. By way of example, but not limitation, episodes such as arrythmias can be detected, either atrial or ventricular, including tachycardia, bradycardia, or fibrillation. Episodes such as these can trigger attempts to deliver therapy, and also trigger storage of diagnostic data, such as EGM data, related in time to the episodes and the delivery of the therapy. Cardiac episodes and therapy delivery attempts are both types of events as used in this description. Although embodiments described herein relate to cardiac episodes, it is to be understood that the invention is not limited to cardiac episodes or events, but may be beneficially applied to other types of events and episodes, such as, but not limited to, low blood sugar episodes, temperature episodes, or others. A system for memory management is described below in which sets of diagnostic data are recorded at times that are around the times of events of interest.

Recording a set of diagnostic data generally refers to storing the diagnostic data at a place in memory 208 where it will not be overwritten or deleted unless a prioritization analysis (discussed below) determines that an episode and its associated set of diagnostic data should be deleted. In this manner, high priority sets of diagnostic data, captured around the times of cardiac events, can be made available to doctors or other medical personnel. In addition, as discussed further below, a time-based association between cardiac episodes and sets of diagnostic data allows for sharing of sets of diagnostic data between events that occur closely in time to one another, thereby eliminating duplicate or redundant sets of diagnostic data in memory 208.

Figure 3:
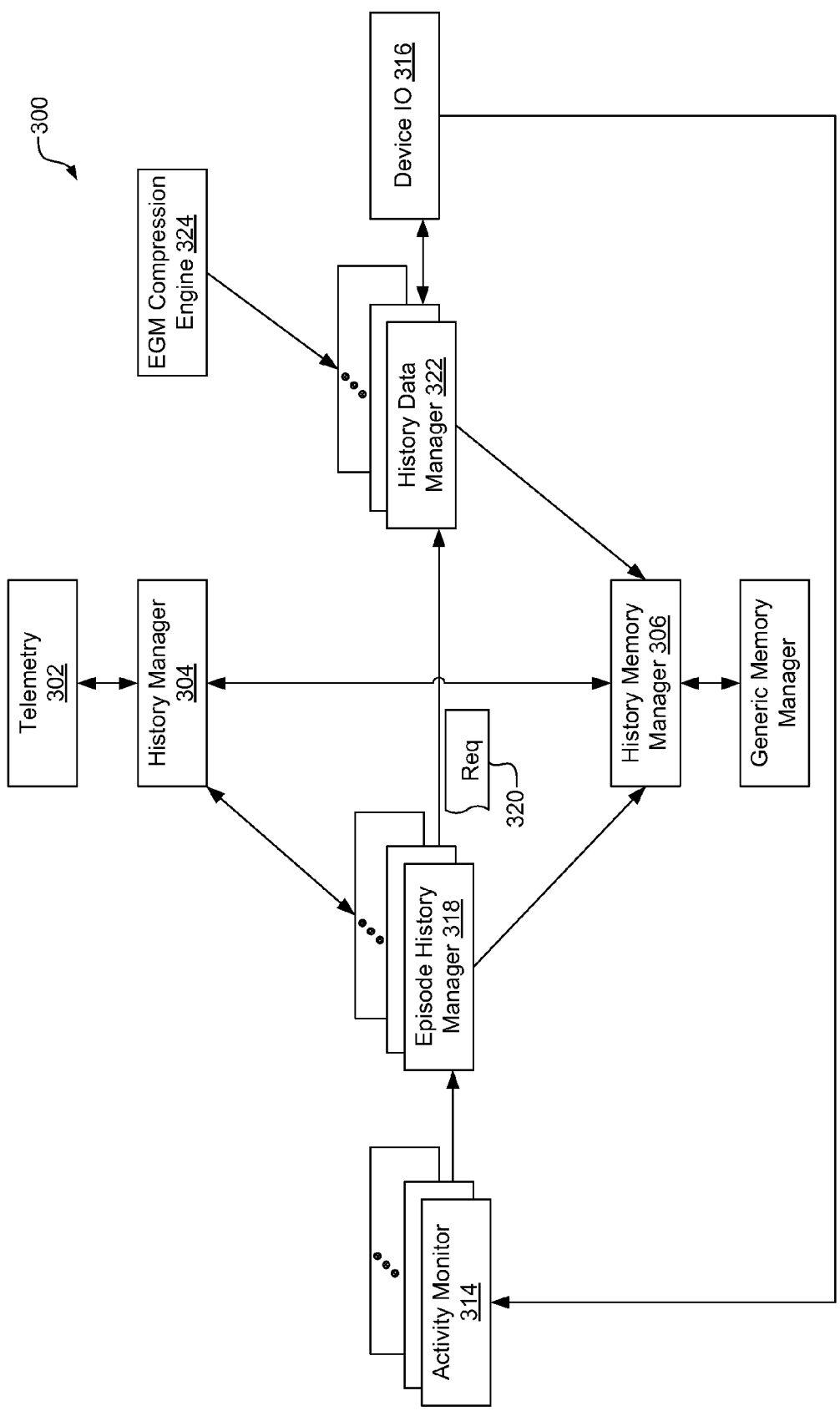
FIG. 3 is a functional block diagram illustrating functional modules included in a therapeutic IMD in accordance with one embodiment.

FIG. 3 is a module diagram illustrating a memory management system 300 that may be implemented in an IMD, such as the ICD 102 (see FIGS. 1-2), to manage memory used for storing diagnostic data related to cardiac events. Part of the process of memory management is determining when to record diagnostic data, and when to stop recording diagnostic data. Another part of the memory management process involves determining whether to delete diagnostic data that was previously recorded in memory to make room for other diagnostic data using an episode priority determination process. Another part of the process involves a lossless diagnostic data compression process using Huffman encoding.

In the embodiment illustrated in FIG. 3, the modules are implemented in software (e.g., software objects, data structures, software programs, etc.). However, the invention is not limited to software implementations, but rather may be implemented in hardware, firmware, or any combination of hardware, software, or firmware.

In general, the system 300 provides for recording sets of diagnostic data around the times of selected events, and time-based association of recorded sets of diagnostic data with the events. In this way, the proper set(s) of diagnostic data can be provided when an episode is later requested by an external device. In addition, the memory management process provides for linking therapy delivery events with corresponding detected episodes so that diagnostic data recorded around the time of the therapy delivery attempts can be associated with the corresponding episode. Sometimes the term "attempt" is used in reference to therapies and non-therapies. Non-therapies are events in which therapy would have been delivered, but for an overriding condition, such as exhaustion of the therapy regimen. Therapy events are deliveries of therapy (e.g., energy delivery in response to an arrhythmia), and include both effective and ineffective therapy deliveries.

The discussion of the memory management system 300 is broken into two general parts: handling requests for event-related diagnostic data from a an external device, and recording sets of diagnostic data in response to events such as cardiac episodes and therapy delivery attempts. Handling the requests from the external device is discussed first, followed by the process of recording sets of diagnostic data.

A telemetry module 302 handles requests for episode-related data from the requesting external device. The request for data identifies the episode. The telemetry module 302 sends the request to a history manager module 304. The history manager module 304 passes the request to a history memory manager 306. The history memory manager 306 determines whether a set of previously recorded diagnostic data is associated with the identified episode by determining whether the time at which the requested episode was detected, or occurred, is within the time spanned by the set of diagnostic data. The history memory manager 306 may identify one or more sets of diagnostic data associated with the requested episode, and provides the diagnostic data to the history manager module 304. The history manager module 304 provides the data to the telemetry module 302, which causes the data to be transmitted to the requesting device.

As discussed above, recording of the sets of diagnostic data is performed around the time of the cardiac episodes. Cardiac episodes are detected by modules referred to as activity monitors 314. Each activity monitor 314 monitors for one or multiple types of episodes. For example, one activity monitor 314 may monitor for ventricular fibrillation, while another activity monitor 314 may monitor for a patient triggered episode. Many other types of activity monitors may be implemented to monitor for many other types of episodes. Some episode types are listed in Table 1 below. When an activity monitor 314 detects occurrence of the episode, the activity monitor 314 triggers recording of diagnostic data by sending a request to an episode history manager 318.

Like each activity monitor 314, each episode history manager 318 corresponds to a type of episode. When an episode is detected, the episode history manager 318 of the appropriate type creates an episode data structure for the detected episode. In general, the episode data structure identifies the episode, the type of episode, start and end timestamp data, and/or other data. During a cardiac episode, a therapy may be initiated by the activity monitor 314 to resolve the cardiac arrhythmia.

Figure 4:
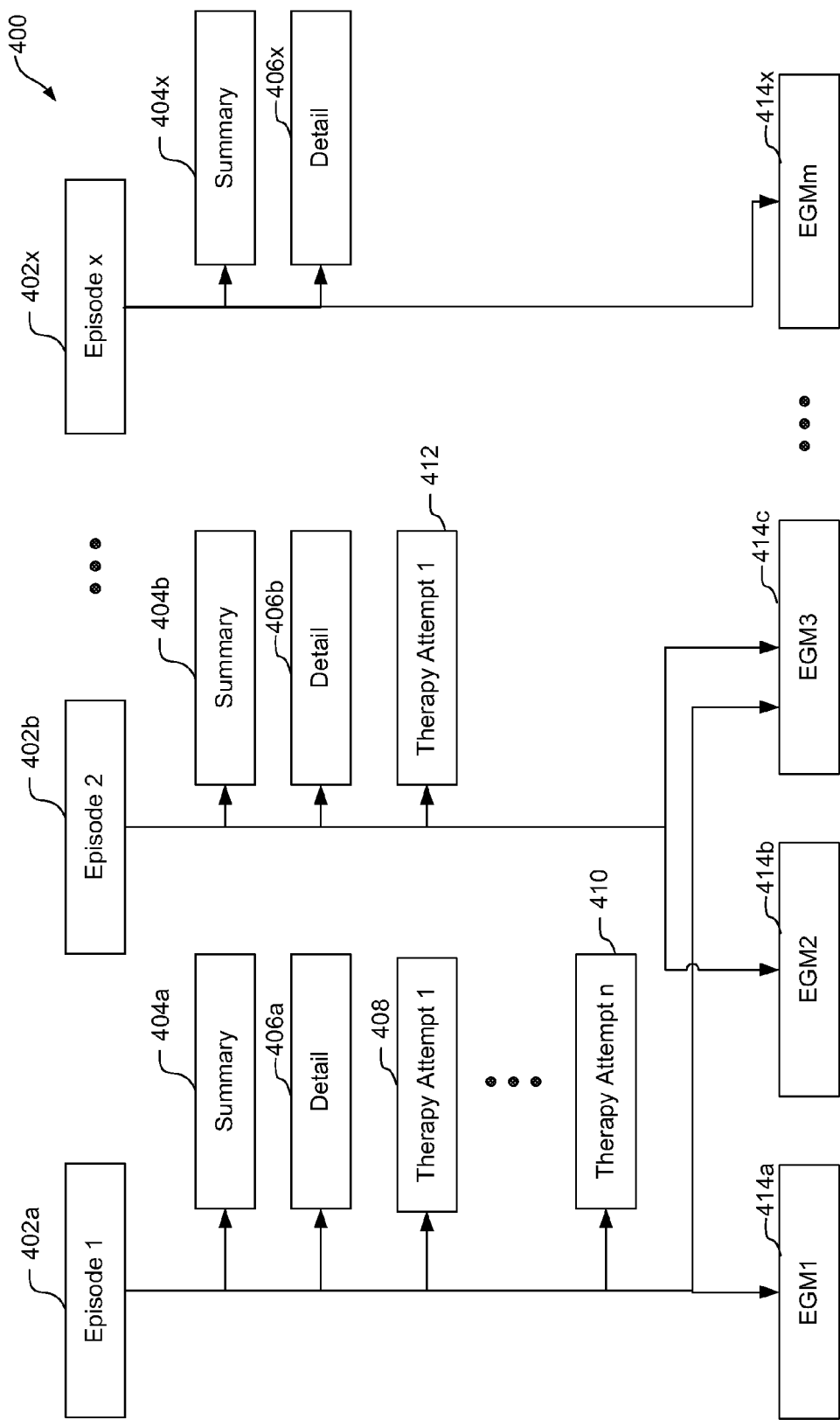
FIG. 4 is a schematic diagram illustrating exemplary data structures and sets of recorded diagnostic data that might be generated by a therapeutic IMD that employs memory management in accordance with one embodiment.

If a therapy attempt is in response to the detected episode, the episode history manager 318 creates an attempt data structure, and links the episode data structure to the attempt data structure. The attempt data structure generally includes an attempt identifier, an attempt type, start and end timestamp data, and/or other data. Exemplary data structures are shown in FIG. 4 and described in detail below. The episode history manager 318 sends the episode data structure and the attempt data structure to the history memory manager 306.

The episode history manager 318 also sends a request 320 to a history data manager 322. The request 320 requests that diagnostic data be recorded, and can specify a time duration for recording. The history data manager 322 begins to stream data to the history memory manager 306, which begins recording the diagnostic data to create a set of diagnostic data in memory. One function of the history data manager 322 is to merge all requests from various episode history managers 318 into one request, and send the single request to the device I/O 316. Based on time information in the request 320, the history data manager 322 stops streaming the diagnostic data at a determined time. The history memory manager 306 stores a start timestamp and an end time stamp associated with each recorded set of diagnostic data, to indicate the start time and the end time of the diagnostic data set, respectively.

Figure 9:
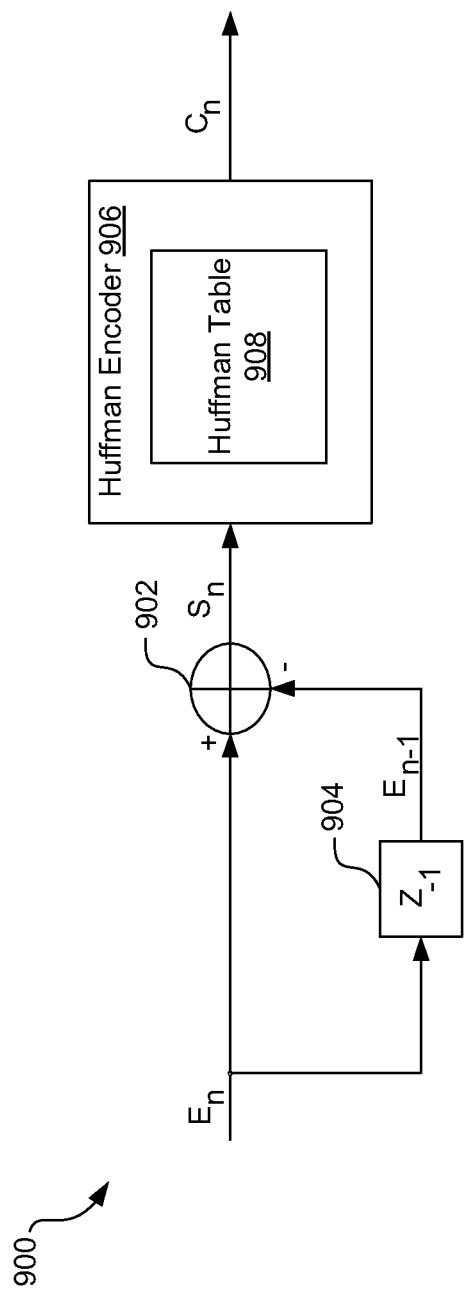
FIG. 9 illustrates components in an exemplary diagnostic data compression engine of an IMD in accordance with one embodiment.

In some embodiments, the history data manager 322 interacts with a diagnostic data compression engine 324 to losslessly compress the diagnostic data. An embodiment of a data compression engine 324 is illustrated in FIG. 9 and discussed below.

The episode history manager 318 also notifies the history manager 304 of interactions between episodes and/or other events. For example, the episode history manager may label concurrent episodes, such as a ventricular episode and an atrial episode, if the episodes have overlapped durations. The concurrent episodes are tagged to show the existence of the other episode(s) to alert the physician as to the other concurrent episode(s).

As discussed above, the history memory manager 306 obtains requested diagnostic data from a set of history data managers 322 that have diagnostic data that has been gathered by the ICD. In the illustrated embodiment, the history memory manager 306 utilizes a general memory manager 326 to manage memory in the IMD. To make good use of limited memory, the history memory manager 306 determines what event-related data to store, and what data to delete when new diagnostic data arrives. In one embodiment, the history memory manager 306 manages the memory using a prioritization schedule, such as is shown Table 1:

TABLE 1

Exemplary Prioritization of Episodes

| Episode Type | Priority | Min # | Max # |
|---|---|---|---|
| VF Episode | 1 | 5 | 10 |
| VT Episode | 2 | 3 | 5 |
| AF Episode | 1 | 5 | 10 |
| AT Episode | 2 | 3 | 5 |
| Non-Sustained V Episode | 3 | 1 | 4 |
| Non-Sustained A Episode | 3 | 1 | 4 |
| Commanded V Episode | 4 | 0 | 2 |
| Commanded A Episode | 4 | 0 | 2 |
| Patient Triggered Episode | 1 | 1 | 1 |
| ATR Episode | 3 | 2 | 5 |
| PMT Episode | 4 | 1 | 3 |
| SBR Episode | 4 | 1 | 3 |
| RMS Episode | 3 | 2 | 5 |

In Table 1 above, there are four columns labeled Episode Type, Priority, Min #, and Max #. The Episode Type column lists a number of types of episodes, including ventricular fibrillation (VF) episode, ventricular tachycardia (VT) episode, atrial fibrillation (AF) episode, atrial tachycardia (AT) episode, non-sustained ventricular episode, non-sustained atrial episode, patient triggered episode, atrial tachycardia response (ATR) episode, pacemaker mediated tachycardia (PMT) episode, sudden bradycardia response (SBR) episode, and reverse mode switch (RMS) episode.

For each episode type in Table 1, there is a priority value listed in the column labeled Priority. The priority value is used to determine which episode data to delete if all memory is being used and another set of episode data is to be stored. Values shown in column Min # indicate a minimum number of sets of episode data that should be kept in memory. Values in Max # indicate a maximum number of sets of episode data that should be stored in memory.

As an example, assume all memory is being used and there are 15 sets of VF episode data stored and 4 sets of SBR episode data stored. If, in this case a VF episode occurs, 1 set of SBR data may be removed in order to make room for the higher priority VF episode data. However, if there are only 2 sets of SBR episode data and 3 sets of PMT episode data, one set of PMT episode data may be deleted to make room for the VF episode data, and the SBR episode data will not be removed, because a minimum of 2 sets of SBR episode data should be maintained if possible.

As another example, if fewer than the minimum number of episodes have been stored for all episode types, then the lowest priority episode is deleted, regardless of whether the fewer than the minimum are stored.

The episode types and the associated values shown in Table 1 are merely for illustrative purposes and are not intended to limit the invention to any particular types of episodes or associated values. Although Table 1 can be reprogrammed through an external device, Table 1 will typically be configured in device memory during manufacture.

FIG. 4 is a schematic diagram illustrating data structures and sets of diagnostic data related to episodes. In this exemplary embodiment, for illustration purposes, it is assumed that the diagnostic data that is recorded is electrogram (EGM) data. However, in other embodiments, other types of diagnostic data may be recorded, such as marker data or sensor data. A number of episode data structures 402a, 402b, . . . , 402x represent episodes that have been detected in an IMD. Each episode data structure 402 includes a summary data structure 404 and a detail data structure 406. The summary data structures 404 include a summary of the episode, which includes an episode type, among other data. The detail data structures 406 include timestamps associated with the episode, among other data.

The episode data structures 402 may also include a link to a therapy attempt data structure. For example, the episode data structure 402a has a link to a first therapy attempt data structure 408. A linked list of therapy attempt data structures is created when there are multiple attempts at therapy delivery for a single episode. Thus, the episode data structure 402a has a link to the first therapy attempt data structure 408, which has a link to another therapy attempt data structure (not shown), and so on, up to a last therapy attempt data structure 410. Each therapy attempt data structure includes data pertaining to the therapy attempt, such as, but not limited to, therapy type, time of therapy, and link to another therapy attempt data structure, if appropriate.

In the embodiment shown in FIG. 4, there are no direct links stored to associate a set of EGM data 414 with its respective episode data structure(s) 402. In this embodiment, EGM data sets 414 are associated with episode data structures 402 using timestamps that are stored in the data structures. Each set of EGM data 414 includes a start timestamp and an end timestamp, indicating when the set of EGM data 414 started being recorded, and when the set of EGM data 414 stopped being recorded, respectively. As such, the start timestamp and the end timestamp of a set of EGM data 414 indicates the time span of the set of EGM data 414.

Each episode has a start timestamp and an end timestamp, which indicate when the episode starts and ends, respectively. The time span of each EGM data 414 is compared with the time span indicated by the timestamp(s) in an episode data structure 402a. If the time span of an EGM data set 414 is within or overlaps with the episode time span, the EGM data is associated with the episode 402a.

In the particular situation shown in FIG. 4, the first EGM data set 414a is associated with the first episode data structure 402a. The second EGM data set 414b is associated with the second episode data structure 402b. The third EGM data set 414c is associated with both the first episode data structure 402a and the second episode data structure 402b. The last EGM data set 414x is associated with only the last episode data structure 402x. The third EGM data set 414c is stored only once in memory and shared between the first episode data structure 402a and the second episode data structure 402b.

Figure 5:
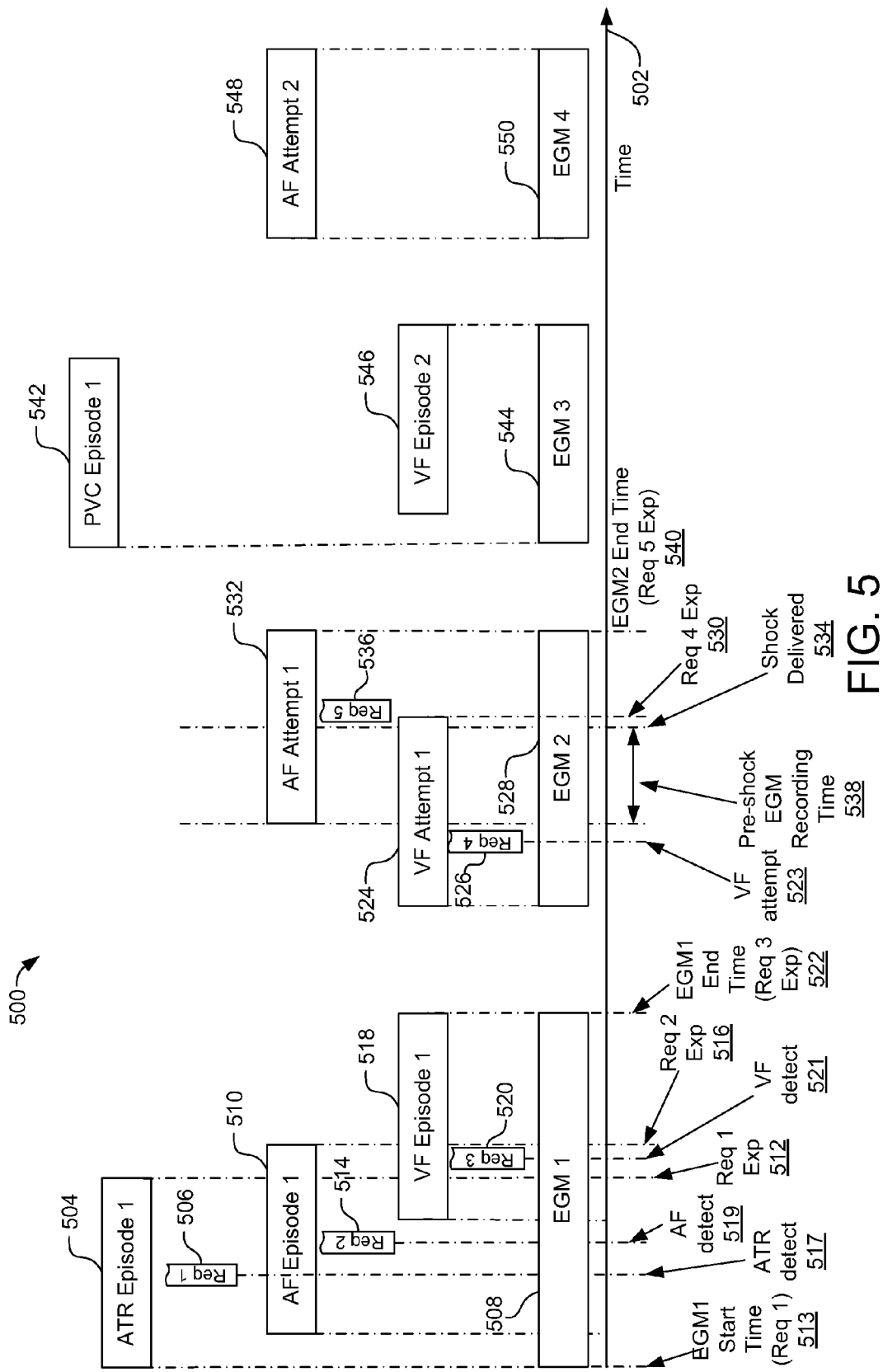
FIG. 5 is a schematic diagram illustrating an exemplary scenario involving recording sets of diagnostic data that are each related to one or more cardiac events.

FIG. 5 depicts an illustrative scenario 500 in which a single set of EGM data is recorded for each set of multiple concurrent cardiac events. Cardiac events include cardiac episodes and therapy delivery attempts. Two events are considered to be concurrent if one event occurs or is detected while diagnostic data is being recorded in response to the occurrence or detection of the other event. Event concurrence can be illustrated with the scenario 500 shown in FIG. 5. In FIG. 5, a time axis 502 is shown at the bottom of the figure to indicate that time progresses from left to right.

When an episode is detected, recording of diagnostic data is triggered. Referring to the system 300 shown in FIG. 3, recording is triggered by issuing a request to the history data manager 322 to begin recording EGM data. The request includes at least one time value indicating the time period or duration for which EGM data should be recorded. Depending on the particular implementation and particular episodes of interest, the requested time durations may vary. In some embodiments, the time durations may vary from 1 second to 20 seconds. The time duration may be specified with a start time and an end time, or with a single end time, or with a value representing a total length of recording time, or otherwise. In some cases, a start time is specified, which may or may not be in the past. If the start time is in the past, diagnostic data can be retrieved from a memory, such as a circular buffer, which keeps a certain amount of past diagnostic data.

A request to record EGM data is said to expire when the time duration specified in the request is reached. If EGM data is already being recorded when a request to record is issued, EGM data will continue to be recorded in the set of EGM data currently being recorded. EGM data will continue to be recorded until expiration of the last request received while recording the set of EGM data. After all requests for recording EGM data have expired while recording a particular set of EGM data, no more EGM data is recorded into that particular set of EGM data. When another request for recording is issued, recording will begin again to form another set of EGM data. All requests involve recording of onset (prior to the event) and post (after the event) data.

To illustrate, the first episode to occur in time in the scenario 500 is an ATR episode, shown with an ATR episode bar 504. When the ATR episode is detected at time 517, a first request 506 is issued to trigger recording of a first set of EGM data 508. The first request 506 specifies a time duration by providing one or more time values. The specified time duration is illustrated by the ATR episode bar 504. The end of the ATR episode bar 504 corresponds to expiration 512 of the first request 506.

In this scenario, the start time 513 for recording of the first set of EGM data 508 is prior to the time of issuance 517 of the first request 506; however, this does not need to be the case in general. In some cases, prior EGM data is not needed as the preconditions of the event are not clinically important. As such, any request can specify a start time prior to the time of issuance of the request. Another approach that can be taken in some embodiments, is to "design in" a specified pre-event time differential. In these embodiments EGM recording will record some EGM data that was received prior to the event, based on the specified time differential prior to issuance of the request.

While the first set of EGM data 508 is being recorded, in this particular scenario, a first atrial fibrillation (AF) episode is detected, illustrated with an AF episode bar 510. When the first AF episode is detected a second request 514 to record EGM data is issued. Because the first set of EGM data 508 is currently being recorded, EGM data continues to be recorded without interruption. However, the second request 514 includes at least one other time value specifying another time duration for which to record EGM data. The time value(s) specified in the second request 514 may specify a later end time than the expiration time 512 of the first request 506. The second time duration is illustrated with the AF episode bar 510. The end of the AF episode bar 510 corresponds to the expiration 516 of the second request 514.

If no other episodes or therapy attempts are detected prior to the expiration 516 of the first AF episode bar 510, then the first set of EGM data 508 would only be recorded until the expiration 516 of the second request 514. However, in the particular scenario 500 illustrated in FIG. 5, another episode is detected prior to the second request's expiration 516. A ventricular fibrillation (VF) episode 518 is detected at time 521, illustrated with a first VF episode bar 518. Detection of the first VF episode causes a third request 520 to be issued. Because EGM data is already being recorded, EGM data continues to be recorded into the first EGM data set 508. The third request 520 includes a third time value that again changes the end time, and hence the time duration, of recording the first set of EGM data 508.

The VF episode bar 518 illustrates the time duration specified in the third request 520. The end of the VF episode bar 518 corresponds to the expiration 522 of the third request 520. In the illustrated scenario 500, no other episodes or therapy delivery attempts are detected prior to the third request's expiration 522. As such, recording of the first set of EGM data 508 ends at the third request's expiration 522.

The ATR episode 504, the AF episode 510, and the first VF episode 518 are concurrent events because each of the events is concurrent with the event that is nearest to it in time. For example, the ATR episode 504 is nearest to the AF episode 510 in time, and the ATR episode 504 is concurrent to the AF episode 510 because the AF episode 510 occurred or was detected while the first set of EGM data 508 was being recorded in response to the ATR episode 504. In addition, the ATR episode 504, the AF episode 510, and the first VF episode 518 are said to be temporally linked to the first set of EGM data 508. More specifically, the ATR episode 504, the AF episode 510, and the first VF episode 518 are said to be multiply temporally linked to the first set of EGM data 508, because these episodes comprise multiple events that are temporally linked to the first set of EGM data 508.

Following the expiration 522 of the third request 520, a VF therapy delivery attempt at time 523, illustrated with a VF attempt bar 524, occurs. The VF therapy delivery attempt 524 is said to be therapeutically linked to the first VF episode 518 because the VF therapy delivery attempt 524 occurred as a result of the VF episode 518, in an attempt to correct the detected ventricular fibrillation of the VF episode 518. The VF attempt 524 issues a fourth request 526 to record EGM data. In response, EGM data begins to be recorded into a second set of EGM data 528.

Prior to the expiration 530 of the fourth request 526 (i.e., the end of the VF attempt bar 524), an AF therapy delivery attempt occurs, illustrated as an AF attempt bar 532. In this case, the AF therapy delivery attempt 532 involves a defibrillation shock, which occurs at a shock delivery time 534. When the AF therapy delivery attempt 532 occurs, a fifth request 536 is issued. The fifth request 536 specifies a pre-shock EGM recording time 538 and an expiration time 540. The pre-shock EGM recording time 538 indicates a time in the past from which to record EGM data.

Because the second set of EGM data 528 is already being recorded, EGM data continues to be recorded into the second set of EGM data 528. It is also determined that the specified pre-shock EGM recording time 538 is within the time span of the second set of EGM data 528, and EGM data for the pre-shock EGM recording time 538 has already been recorded. Therefore, in this particular case, there is no need to record past EGM data when the fifth request 536 is received. However, in other scenarios, there may be a need go back to prior received EGM data and record EGM data starting from a specified prior time, if the requested past data has not already been recorded. It is noted that the AF attempt 532, the first VF attempt 524, and the second set of EGM data 528 are multiply temporally linked.

In the particular exemplary scenario 500 of FIG. 5, after the expiration 540 of the fifth request 536, a PVC episode occurs, as illustrated by a PVC episode bar 542. A request (not shown) is issued to begin recording EGM data. While a third set of EGM data 544 is being recorded in response to the PVC episode, a second VF episode occurs, illustrated with a second VF episode bar 546. Another request (not shown) is issued, which causes the EGM recording to continue past the expiration of the PVC episode request. The PVC episode 542 and the second VF episode 546 are multiply temporally linked.

Sometime after recording the third set of EGM data 544, a second AF attempt occurs, which is illustrated as a second AF attempt bar 548. In response to the second AF attempt 548, another request (not shown) is issued to begin recording a fourth set of EGM data 550. In this case, no other events occur during recording of the fourth set of EGM data 550. As such, the second AF attempt 548 is said to be singly temporally linked to the fourth set of EGM data 550. In addition, the second AF attempt 548 occurred as a result of the AF episode 510. The AF episode 510, the first AF attempt 532, and the second AF attempt 548 are said to be therapeutically linked. As discussed above, data structures can be created that create associations between therapeutically linked events, such as cardiac episodes, and therapy delivery attempts.

Figure 6:
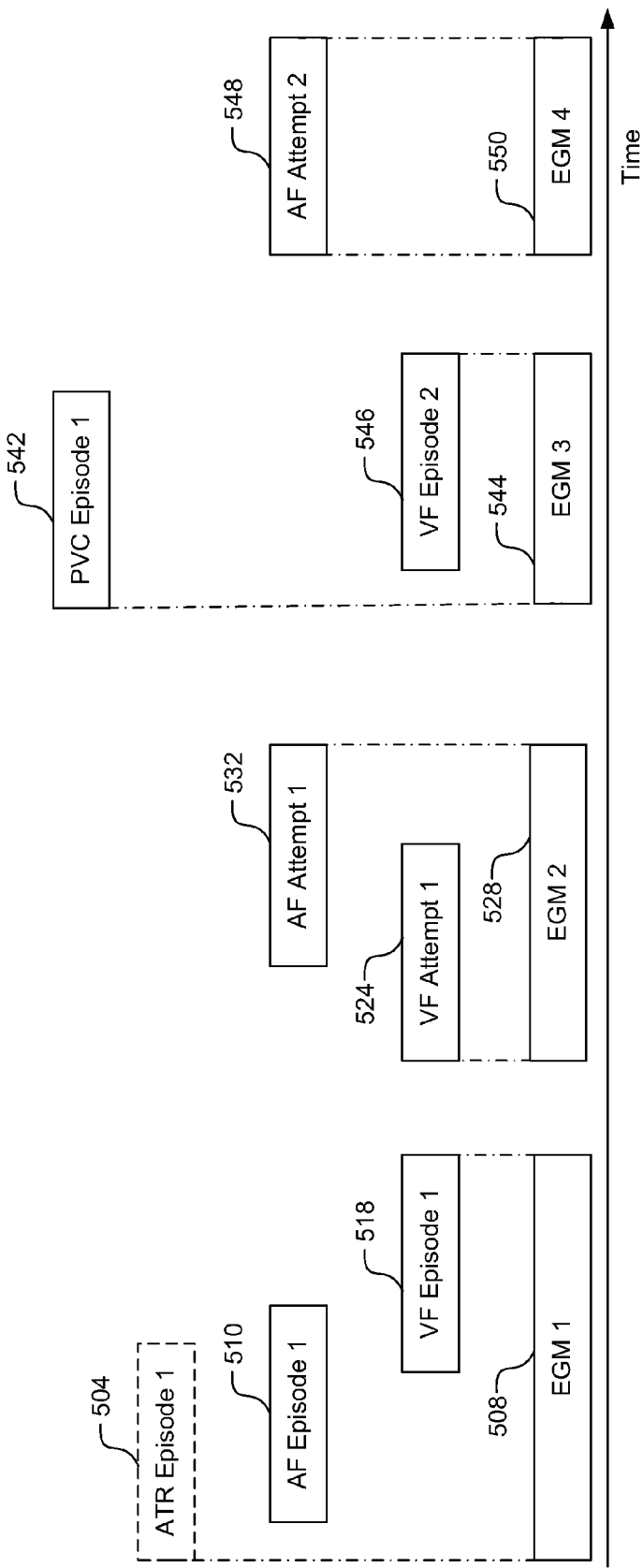
FIGS. 6-8 are schematic diagrams illustrating scenarios involving deleting from memory one or more of the sets of selected diagnostic data recorded in the scenario of FIG. 5.
Figure 7:
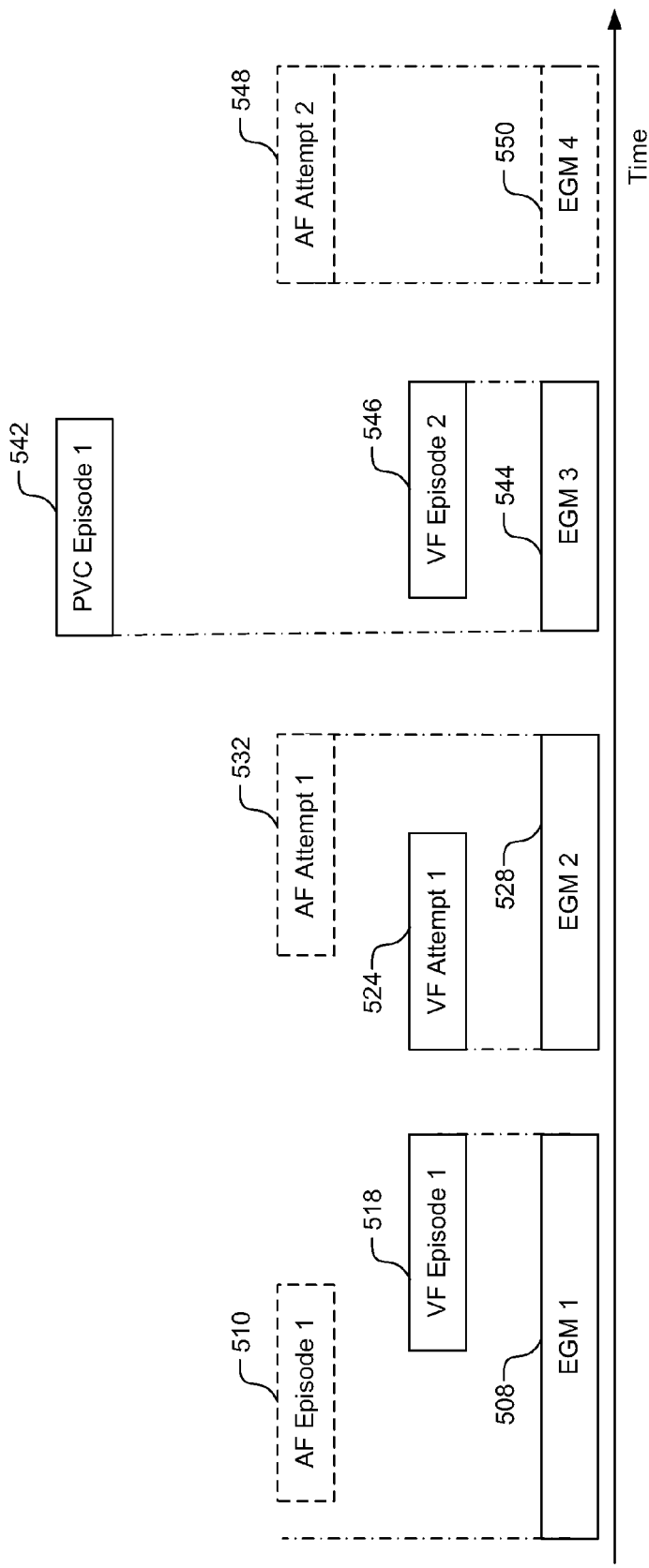
Figure 8:
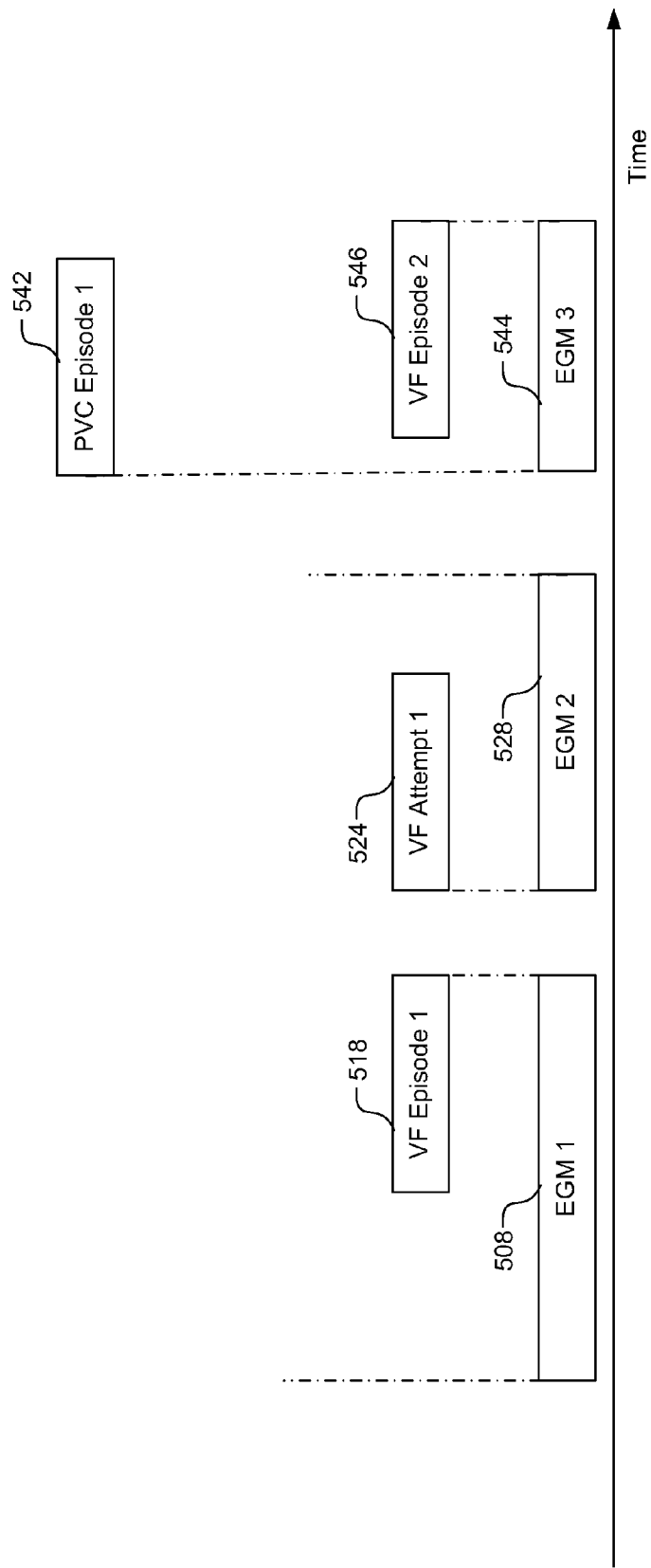

FIGS. 6-8 illustrate a scenario in which event-related diagnostic data is deleted from memory in accordance with various embodiments of the present invention. As discussed herein, in some embodiments diagnostic data for lower priority events or older events may be deleted to make room for higher priority or more recent event data. The scenario illustrates a data deletion process that can be employed to make memory available in an IMD. Deleting data from memory includes overwriting the data or removing the data from memory in any way. Generally, when an event is to be removed from memory, all diagnostic data that is singly temporally linked with the event, as well as diagnostic data that is singly temporally linked with events that are therapeutically associated with the event, and their corresponding data structures are removed.

FIG. 6 illustrates a scenario of deleting an ATR episode. The deletion of the ATR episode is shown using dotted lines for the ATR episode bar 504. The ATR episode 504 is associated in time with the first set of recorded EGM data 508. Also associated with the first set of EGM data 508 are the AF episode 510 and the VF episode 518. The ATR episode 504 is not singly linked to the first set of EGM data 508, or any other set of recorded EGM data. In addition, the ATR episode 504 is not associated with any other events. Consequently, removing the ATR episode 504 does not involve removing any recorded diagnostic data. However, removing the ATR episode 504 involves removing any data structures that were created for the ATR episode 504.

FIG. 7 illustrates a scenario of deleting the AF episode 510. The AF episode 510 is associated in time with the first set of EGM data 508, as is the first VF episode 518. Therefore, the AF episode 510 is multiply temporally associated with the first set of EGM data 508, and the first set of EGM data 508 is not removed from memory. The AF episode 510 is therapeutically linked with two other events: the first AF therapy delivery attempt 532 and the second AF therapy delivery attempt 548. Because they are therapeutically linked with the AF episode 510, the first AF therapy delivery attempt 532 and the second AF therapy delivery attempt will also be removed from memory 548. In addition, any set(s) of recorded diagnostic data that are singly temporally linked with either of the first AF therapy delivery attempt 532 and the second AF therapy delivery attempt 548, will be removed.

The first AF therapy delivery attempt 532 is temporally linked with the second set of EGM data 528. The VF therapy delivery attempt 524 is also temporally linked with the second set of EGM data 528. As such, the first AF therapy delivery attempt 532 is multiply temporally linked, and not singly temporally linked, with the second set of EGM data 528. The second set of EGM data 528 is therefore not removed from memory.

The second AF therapy attempt 548 is temporally linked with the fourth set of EGM data 550. No other events are temporally linked with the fourth set of EGM data 550. As such, the second AF therapy attempt 548 is singly linked with the fourth set of EGM data 550. The fourth set of EGM data 550 is therefore removed as a result of removal of the second AF therapy attempt 548. The removal of the fourth set of EGM data 550 is illustrated with dotted lines; the removal of other data related to the second AF attempt 548 is illustrated with dotted lines for the second AF attempt bar 548.

FIG. 8 illustrates the result of the data removal in the scenarios shown in FIG. 6 and FIG. 7. The ATR episode 504, the AF episode 510, the first AF attempt 532, the second AF attempt 548, and the fourth set of EGM data 550 have been removed. In this scenario, data structures corresponding to the ATR episode 504, the AF episode 510, the first AF therapy delivery attempt 532, and the second AF therapy delivery attempt 548 have been deleted from memory, and the fourth set of EGM data 550 has also been deleted from memory.

FIG. 9 illustrates an exemplary compression engine 900 for compressing diagnostic data in accordance with one embodiment. In this embodiment, the source data is periodically read out from the circular buffer and stored in an internal intermediate buffer. The compression algorithm is applied to each sample of data in the intermediate buffer and the compressed data is stored in another memory space for long term storage. A header is applied to the compressed data, which indicates the algorithm used to compress the data and resulting compressed size.

In general, the embodiment of FIG. 9 employs first order differential pulse code modulation (DPCM) with Huffman encoding. Original data samples, $E_n$, are input to the compression engine. $E_n$ are samples from an 8-bit EGM signal sampled at a selected frequency, such as, but not limited to 200 Hz, where n is greater than or equal to zero. $E_n$ are input into a difference module 902 and a delay 904. The output of the delay is $E_{n-1}$. The difference module 902 subtracts each $E_{n-1}$ from each $E_n$. The output of the difference module 902 is $S_n$, which is the first order derivative of $E_n$. $S_n$ is input into a Huffman encoder 906. The Huffman encoder 906 uses a Huffman encoding table 908 that includes a code word for each $S_n$. $C_n$ is the encoded code word found by looking up $S_n$ in the Huffman encoding table 908.

The Huffman encoding table 908 is predetermined from analysis of a multi-patient database. In accordance with at least one embodiment, the same Huffman encoding table 908 is used for all EGM channels (e.g., atrial, ventricular, etc.), and is not stored with the EGM data. In testing it has been found that at least a 2:1 compression ratio can be achieved.

Exemplary Operations

Figure 10:
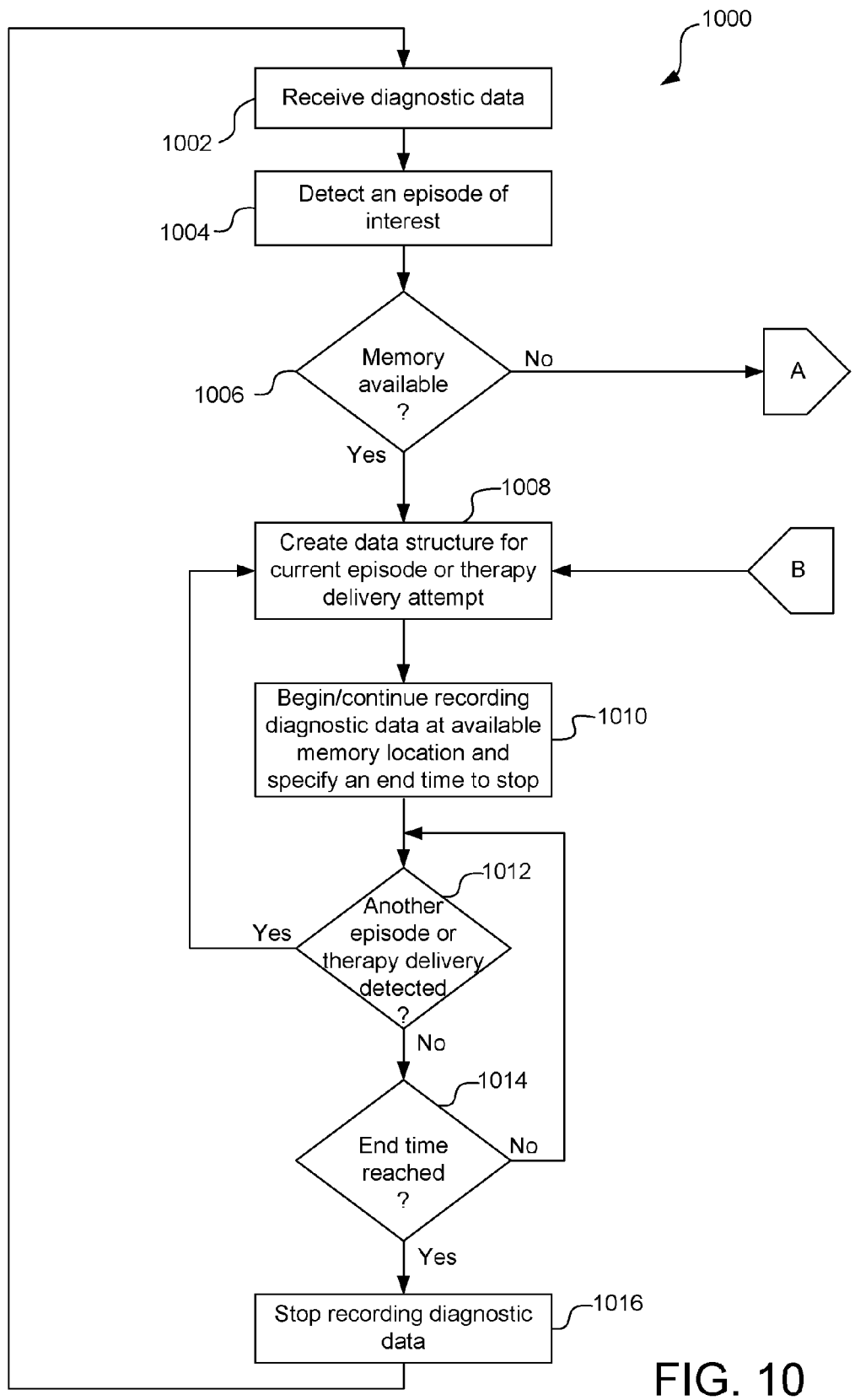
FIG. 10 is a flow chart illustrating an algorithm that can be carried out by an IMD to carry out time-based diagnostic data management in accordance with one embodiment.

FIG. 10 is a flow chart illustrating an algorithm 1000 that can be carried out by a therapeutic IMD to carry out time-based diagnostic data management in accordance with one embodiment. In some embodiments, the algorithms 1000 and 1100 (FIG. 11) are carried out as software threads. In these embodiments, each event may execute an associated thread, which records data for that event.

In this embodiment, throughout the algorithm 1000 the IMD receives diagnostic data via leads of the IMD in a substantially continuous fashion. In one embodiment, the received diagnostic data is stored in a circular buffer temporarily from which it can be retrieved and recorded. Because the data is stored in a circular buffer, it is typically possible to retrieve some amount of past diagnostic data, which may be recorded for analyzing preconditions prior to an event such as therapy delivery. The circular buffer is only temporary memory and the data therein will be written over when the buffer is full and as new diagnostic data is received. The size of the buffer dictates how long diagnostic data resides in the circular buffer before getting overwritten and how far back in time diagnostic data can be retrieved.

The algorithm 1000 generally determines when to record (e.g., save in a more permanent memory) diagnostic data based on events that occur. Received diagnostic data is analyzed to monitor for physiologic events of interest. A detecting operation 1004 detects a physiologic event of interest. The detecting operation 1004 triggers a process for gathering and generating data related to the event. A query operation 1006 determines whether sufficient memory is available for storing the event-related data. The query operation 1006 may test memory to determine if there is available memory above a certain sufficiency threshold. If the query operation determines that insufficient memory is available, the algorithm 1000 branches "No" to a memory reallocation operation shown in FIG. 11, and described below.

If the query operation 1006 determines that sufficient memory is available, the algorithm 1000 branches "Yes" to a creating/updating operation 1008. The creating operation 1008 creates one or more data structures for the detected event. In some embodiments, the created data structures include a summary data structure and a detail data structure. The summary data structure provides a high-level summary of various aspects of the event, such as the event type. The detail data structure provides more detail, such as the start time or detection time of the event, as well as the end time of the event. The detail data structure may also store a time value corresponding to a time span of diagnostic data to be captured.

A recording operation 1010 begins recording diagnostic data at the available memory location. The recording operation 1010 copies or moves diagnostic data from the circular buffer to another part of memory for longer term storage. The recording operation 1010 may optionally specify an end time, at which recording of diagnostic data is to end. The recording end time may be specified as an absolute time, or as a time relative to the current time, or otherwise.

Another query operation 1012 determines whether another event, such as therapy delivery, has occurred prior to the specified recording end time. If another event has occurred, the algorithm 1000 branches "Yes" back to the creating/updating operation 1008. The creating/updating operation 1008 creates another one or more data structures for storing data related to the new event or updates an existing data structure.

If the query operation 1012 determines that another event has not occurred, the algorithm 1000 branches "No" to another query operation 1014. The query operation 1014 determines whether the event has ended. If the specified recording end time has not been reached, the algorithm branches "No" back to the query operation 1012, which again checks whether another event has occurred.

If the query operation 1014 determines that the event has ended, the algorithm branches "Yes" to another query operation 1016. The query operation 1016 determines whether more than the specified maximum number of events of the current event type have been recorded. If the maximum number of events of the current event type have been recorded, the algorithm 1000 branches "Yes" to a deleting operation 1018, which deletes the oldest event data of the event type. If the maximum number of event data sets have not been recorded for the current event type, the algorithm 1000 branches "No" to the detecting operation 1004, which waits to detect another event.

Figure 11:
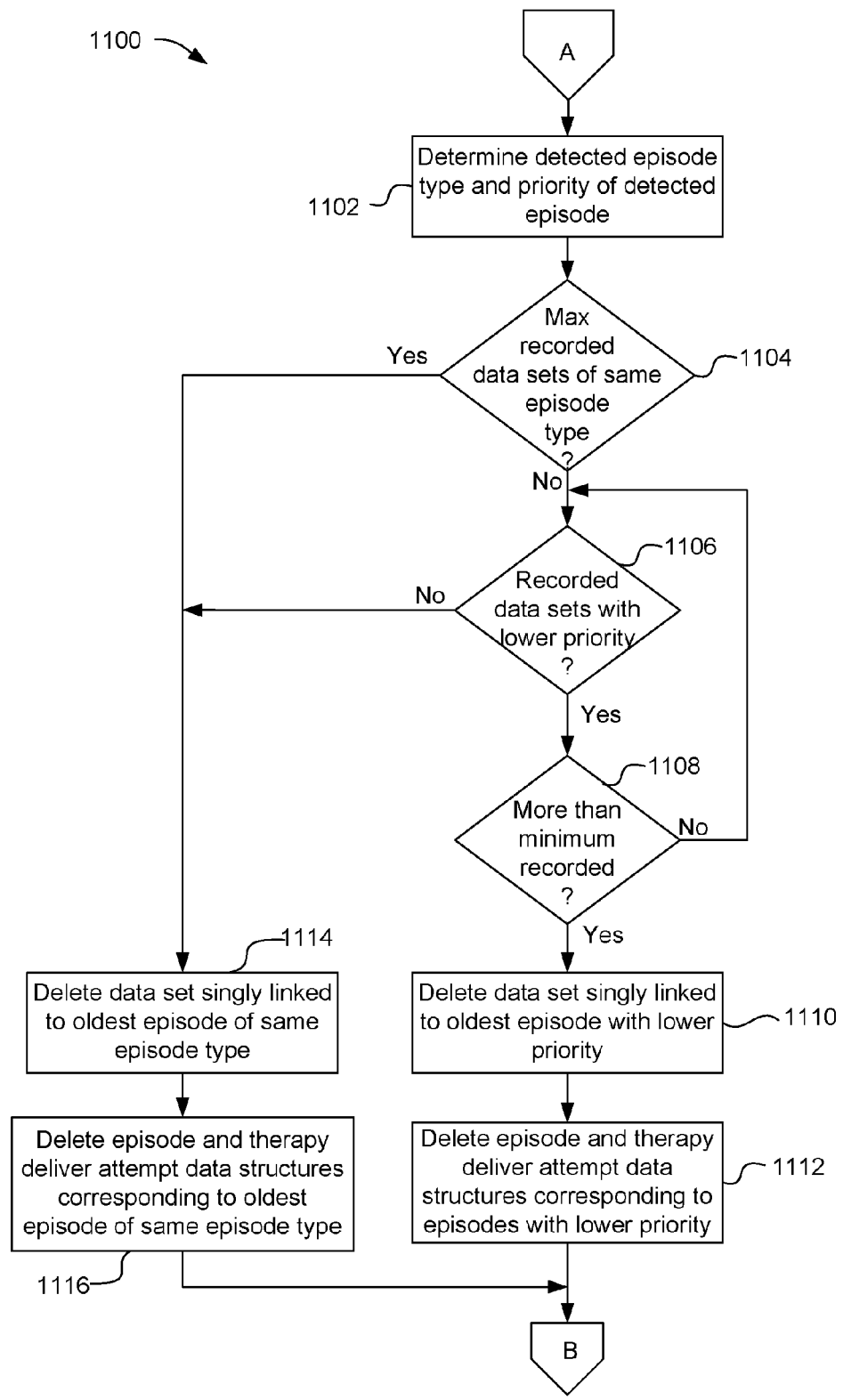
FIG. 11 is a flowchart illustrating an algorithm that can be carried out by an IMD for managing memory based on an episode prioritization schedule with specified minimums and maximums.

FIG. 11 is a flowchart illustrating an algorithm 1100 that can be carried out by a therapeutic IMD for allocating diagnostic data memory based on an event prioritization schedule with specified minimum numbers of event types and maximum numbers of event types. As discussed above, entry to the algorithm 1100 is made through the algorithm 1000 shown in FIG. 10, when an event has been detected, but there is insufficient memory available.

Initially, a searching operation 1102 searches from low to high priority for an event type for which events have been recorded and for which more than the specified minimum number of events have been recorded. Exemplary event types with associated priorities are shown above in Table 1. Such a table could be stored in memory and used in the searching operation 1102. In a query operation 1104, it is determined whether any events were found in the searching operation 1102 above the minimum specified number.

A deleting operation 1106 deletes the diagnostic data recorded for the oldest event of the found (in operation 1102) priority event type above the specified minimum for that event type. The deleted diagnostic data includes diagnostic data sets that are singly temporally linked with therapy delivery attempts that are therapeutically linked to the episode of the same type.

A query operation 1108 then determines if enough memory has been freed. If not, the algorithm branches "No" to the searching operation 1102. The algorithm 1100 loops through the searching operation 1102, the query operation 1104, the deleting operation 1106 and the query operation 1108 until the query operation 1104 determines that no remaining events of any priority have been recorded above the minimum specified number.

After memory associated with events above the specified minimum have been deleted, if more memory is still needed, the algorithm 1100 branches to another searching operation 1110. The searching operation 1110 searches from low to high priority for an event type for which events have been recorded, regardless of whether more than the specified minimum have been stored. A deleting operation 1112 deletes the oldest recorded event for the found priority event type, including singly linked data sets and therapy delivery attempts.

Another query operation 1114 determines whether enough memory has been freed by the algorithm 1100. If not, the algorithm 1100 continues to loop through the searching operation 1110, the deleting operation 1112, and the query operation 1114, until enough memory has been freed.

Figure 12:
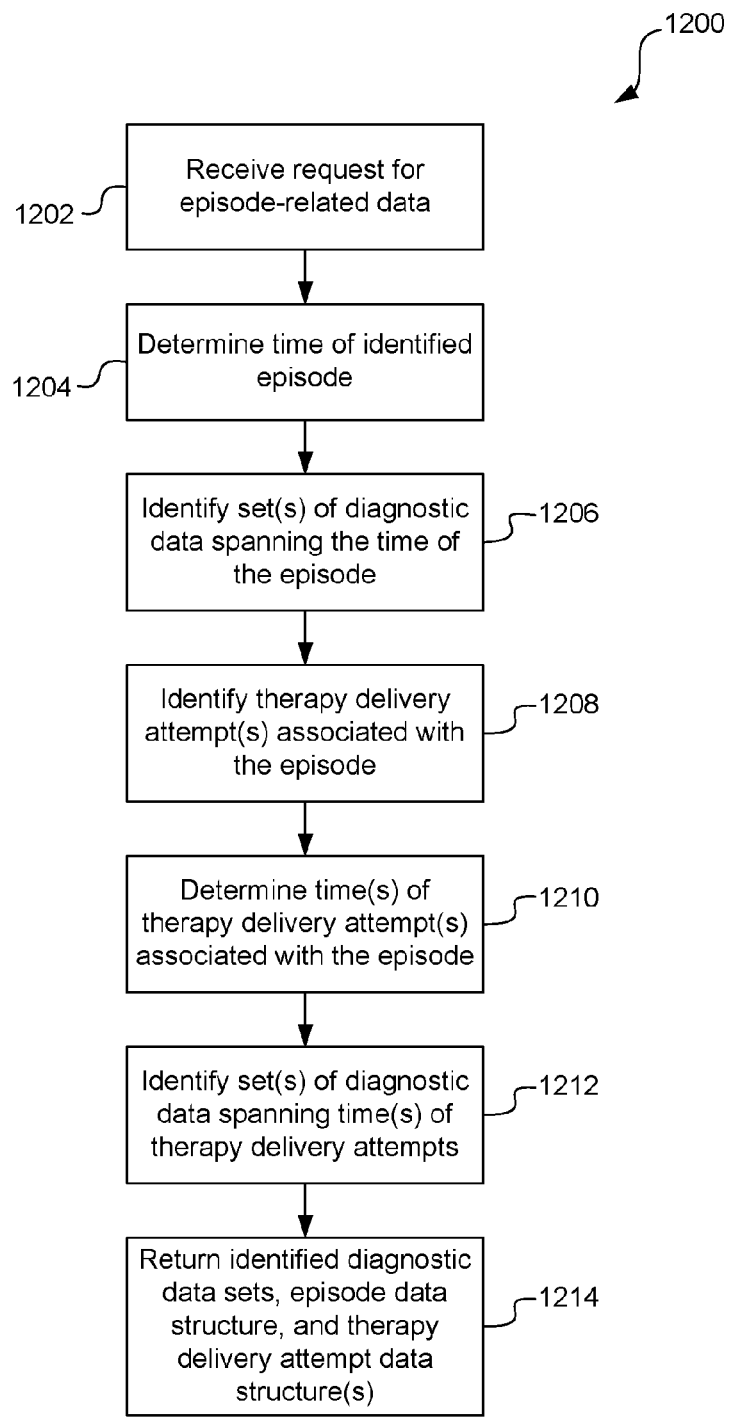
FIG. 12 is a flowchart illustrating an algorithm that can be carried out by an IMD for providing episode-related data in response to a request for the data.

FIG. 12 is a flowchart illustrating an algorithm 1200 that can be carried out by a therapeutic IMD for providing episode-related data in response to a request for the data. Initially, a request is received in a receiving operation 1202. The request is typically transmitted by the external device and specifies an episode for which episode-related data is desired. A determining operation 1204 determines the time of the specified episode. An episode identifier is used to access a corresponding episode data structure. The data structure has stored in it one or more times associated with the episode. Using the time(s) in the data structure, the determining operation 1204 determines when the episode occurred or was detected.

An identifying operation 1206 identifies one or more sets of diagnostic data that was recorded around the time of the specified episode. More specifically, the identifying operation 1206 identifies recorded diagnostic data sets that span the time of the episode. The recorded data sets have timestamps indicating their start times and their end times. Using the timestamps, relevant diagnostic data sets can be identified.

Another identifying operation 1208 identifies any therapy delivery attempts that are associated with the specified episode. In accordance with one embodiment, therapy delivery attempt data structures would have been created for any therapy delivery attempts, and they would have been linked to an episode via a link in an episode data structure. Multiple therapy delivery attempt data structures are associated through a linked list. Using the links, the identifying operation 1208 can identify any therapy delivery attempts that occurred in response to the specified episode.

A determining operation 1210 determines the time or times of the identified therapy delivery attempts. Timestamps stored in associated therapy delivery data structures can be used by the determining operation 1210 to determine the times of the identified therapy delivery attempts. Another identifying operation 1212 identifies any sets of recorded diagnostic data that span the time or times of the identified therapy delivery attempts.

A returning operation 1214 returns data related to the requested episode. In one embodiment, the returning operation 1214 returns the episode data structure summary, the episode data structure detail, the linked therapy attempt data structure details, and any sets of diagnostic data that are singly or multiply linked to the requested episode.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A method for processing data in an implantable medical device (IMD), the method comprising:

generating physiological data from signals received from one or more leads associated with the IMD;

sampling the physiological data to generate a plurality of data samples;

applying a linear predictive encoding algorithm having a first order derivative calculation to the plurality of data samples to generate a plurality of encoded data samples each corresponding to one of the plurality of data samples;

applying an entropy encoding algorithm to the plurality of encoded data samples to generate a plurality of code words each corresponding to one of the plurality of encoded data samples; and storing the code words in a memory in the IMD.

2. The method of claim 1, wherein applying a linear predictive encoding algorithm to the plurality of data samples comprises applying a differential pulse code modulation on the plurality of data samples.

3. The method of claim 1, wherein applying an entropy encoding algorithm to the plurality of encoded data samples applying a Huffman encoding algorithm to the plurality of encoded data samples.

4. The method of claim 3, wherein applying the Huffman encoding algorithm to the plurality of encoded data samples comprises associating each encoded data sample with a code word in a Huffman encoding table.

5. The method of claim 4, wherein the physiological data from each of the one or more leads is encoded using the same Huffman encoding table.

6. The method of claim 1, wherein the applied entropy encoding algorithm is based on an analysis of a multi-patient database.

7. The method of claim 1, wherein the sampling step comprises:

sampling the physiological data at a sampling frequency.

8. The method of claim 7, wherein sampling the physiological data at the sampling frequency comprises:

periodically reading a data sample from a circular buffer; and storing the data sample in an intermediate buffer.

9. An implantable medical device (IMD) comprising:

one or more leads configured to sense physiological signals;

a processor configured to:
- generate physiological data from the physiological signals received from one or more leads associated with the IMD;
- sample the physiological data to generate a plurality of data samples;
- apply a predictive encoding algorithm to the plurality of data samples to generate a plurality of encoded data samples each corresponding to one of the plurality of data samples; and
- apply an entropy encoding algorithm to the plurality of encoded data samples to generate a plurality of code words each corresponding to one of the plurality of encoded data samples; and a memory configured to:
- to store the physiological data in a circular buffer;
- to store the physiological data sample in an intermediate buffer; and
- store the code words.

10. The IMD of claim 9, wherein the predictive encoding algorithm comprises a linear predictive encoding algorithm.

11. The IMD of claim 10, wherein the linear predictive encoding algorithm comprises a differential pulse code modulation.

12. The IMD of claim 9, wherein the entropy encoding algorithm comprises a Huffman encoding algorithm.

13. The IMD of claim 12, wherein applying the Huffman encoding algorithm to the plurality of encoded data samples comprises associating each encoded data sample with a code word in a Huffman encoding table.

14. The IMD of claim 13, wherein the physiological data from each of the one or more leads is encoded by the processor using the same Huffman encoding table.

15. An implantable medical device (IMD) comprising:

a memory configured to store a prioritization schedule of physiological episodes, wherein the prioritization schedule specifies a priority for each of a plurality of types of physiological episodes, a minimum number indicating a minimum number of data sets to be recorded for each of the physiological episodes, and a maximum number indicating a maximum number of data sets to be recorded for each of the physiological episodes; and a processor configured to delete a first recorded set of diagnostic data associated with a type of physiological episode of a first priority, only if a second received set of diagnostic data is associated with a type of physiological episode of a second priority that is higher than the first priority, and deletion of the first set of diagnostic data would not result in fewer sets of diagnostic data than the minimum number specified for the type of episode associated with the first set of diagnostic data.

16. The IMD of claim 15, wherein the processor is further configured to delete the first set of diagnostic data only if fewer than the maximum number of sets of diagnostic data specified for the type of episode associated with the second set of diagnostic data have been recorded.

17. The IMD of claim 15, wherein the processor is further configured to compress each set of diagnostic data using differential pulse code modulation (DPCM) and Huffman encoding.

* * * * *